United States Patent [19]

Anderson

[11] Plant 4,076

[45] July 12, 1977

[54] NECTARINE TREE

[75] Inventor: Fredric W. Anderson, Merced, Calif.

[73] Assignee: Stark Bro's Nurseries and Orchards Co., Louisiana, Mo.

[21] Appl. No.: 717,465

[22] Filed: Aug. 24, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is large, vigorous, upright to spreading, open, foliated with large to medium, lanceolate, acutely pointed leaves having a glandular, crenate margin, blooms with large pink flowers, and is a regular and productive bearer of large to medium, uniform, symmetrical, globose to oblong, freestone fruit having yellow skin overspread with red, and yellow flesh.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard located as aforesaid, as a cross between the Red Diamond nectarine (U.S. Plant Pat. No. 3,165) as the seed parent, and the May Grand nectarine (U.S. Plant Pat. No. 2,794) as the pollen parent. In maturity, such cross evidenced certain novel and distinctive characteristics desirable for a commercially grown nectarine, and I, therefore, undertook asexual reproduction of it preparatory to introduction to the trade.

ASEXUAL REPRODUCTION OF THE VARIETY

I asexually reproduced the present variety of nectarine tree by top-working the same on mature orchard trees located in my said experimental orchard, and such reproductions were found to run true to the original tree in all respects.

SUMMARY OF THE VARIETY

The herein claimed new and distinct variety of nectarine tree is large, vigorous, upright to spreading, open, foliated with large to medium, lanceolate, acutely pointed leaves having a glandular, crenate margin, blooms with large pink flowers, and is a regular and productive bearer of large to medium, uniform, symmetrical, globose to oblong, freestone fruit having yellow skin overspread with red, and yellow flesh; the variety being particularly characterized by fruit of good to best eating quality, which has the firmness and good shipping qualities of the seed parent, Red Diamond nectarine, but ripens with the pollen parent, May Grand nectarine.

BRIEF DESCRIPTION OF THE DRAWING

The drawing is an illustration, by photographic reproduction in color, of leaves and fruit of the variety; one fruit being partially cut away to expose the flesh.

DESCRIPTION OF THE VARIETY

The botanical details of this new and distinct variety of nectarine tree — with color definitions (except those in common color terms) referenced to Maerz and Paul Dictionary of Color — are as follows:

Tree:
- *Size.*—Large.
- *Vigor.*—Vigorous.
- *Growth.*—Upright to spreading.
- *Density.*—Open.
- *Production.*—Productive.
- *Bearing.*—Regular bearer.

Trunk:
- *Size.*—Medium.

Branches:
- *Size.*—Medium.

Leaves:
- *Size.*—Large to medium; average length — 5½"; average width — 1⅜".
- *Form.*—Lanceolate; acutely pointed.
- *Thickness.*—Medium.
- *Margin.*—Glandular; crenate.
- *Petiole.*—Medium length — average ½"; medium thickness.
- *Glands.*—Average number and position — 2 on petiole and 2 on blade; medium size; reniform.
- *Color.*—Top side — Medium green (23-L-8); under side — Lighter green (22-L-6).

Flowers:
- *Blooming period.*—Medium, as compared with other varieties.
- *Size.*—Large.
- *Color.*—Pink.

Fruit:
- *Maturity when described.*—Eating ripe — June 30, 1976.

*Date of first picking.*—June 18, 1976.
*Date of last picking.*—June 28, 1976.
*Size.*—Uniform; large to medium; average diameter axially — 2⅜"; average transversely in suture plane — 2 5/16".
*Form.*—Uniform; symmetrical; globose to oblong.
*Suture.*—Distinct; shallow; extends from base to apex, with slight depression beyond pistil point.
*Cavity.*—Circular.
*Base.*—Rounded.
*Apex.*—Short; depressed.

Skin:
*Thickness.*—Medium.
*Texture.*—Tough.
*Tenacity.*—Parts easily from flesh.
*Tendency to crack.*—None noted.
*Down.*—Wanting.
*Color.*—Yellow (9-L-6) substantially overspread with red (6-L-4) shading darker to 7-L-6, with yellow flecks.

Flesh:
*Juice.*—Moderate; rich.
*Texture.*—Firm; crisp.
*Ripens.*—Evenly.
*Flavor.*—Subacid; delicate.
*Eating quality.*—Good to best.
*Color.*—Yellow (9-L-4).
*Surface of pit cavity.*—Yellow (9-L-3).

Stone:
*Type.*—Free.
*Size.*—Medium; average length — 1¼"; average breadth — 1"; average thickness — ⅝".
*Form.*—Oval.
*Sides.*—Equal.
*Tendency to split.*—Slight.
*Kernel.*—Sweet.
*Color.*—Beige (11-J-6).

Use: Market — local. Dessert.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, upright to spreading, open, foliated with large to medium, lanceolate, acutely pointed leaves having a glandular, crenate margin, blooms with large pink flowers, and is a regular and productive bearer of large to medium, uniform, symmetrical, globose to oblong, freestone fruit having yellow skin overspread with red, and yellow flesh; the variety being particularly characterized by fruit of good to best eating quality, which has the firmness and good shipping qualities of the seed parent, Red Diamond nectarine, but ripens with the pollen parent, May Grand nectarine.

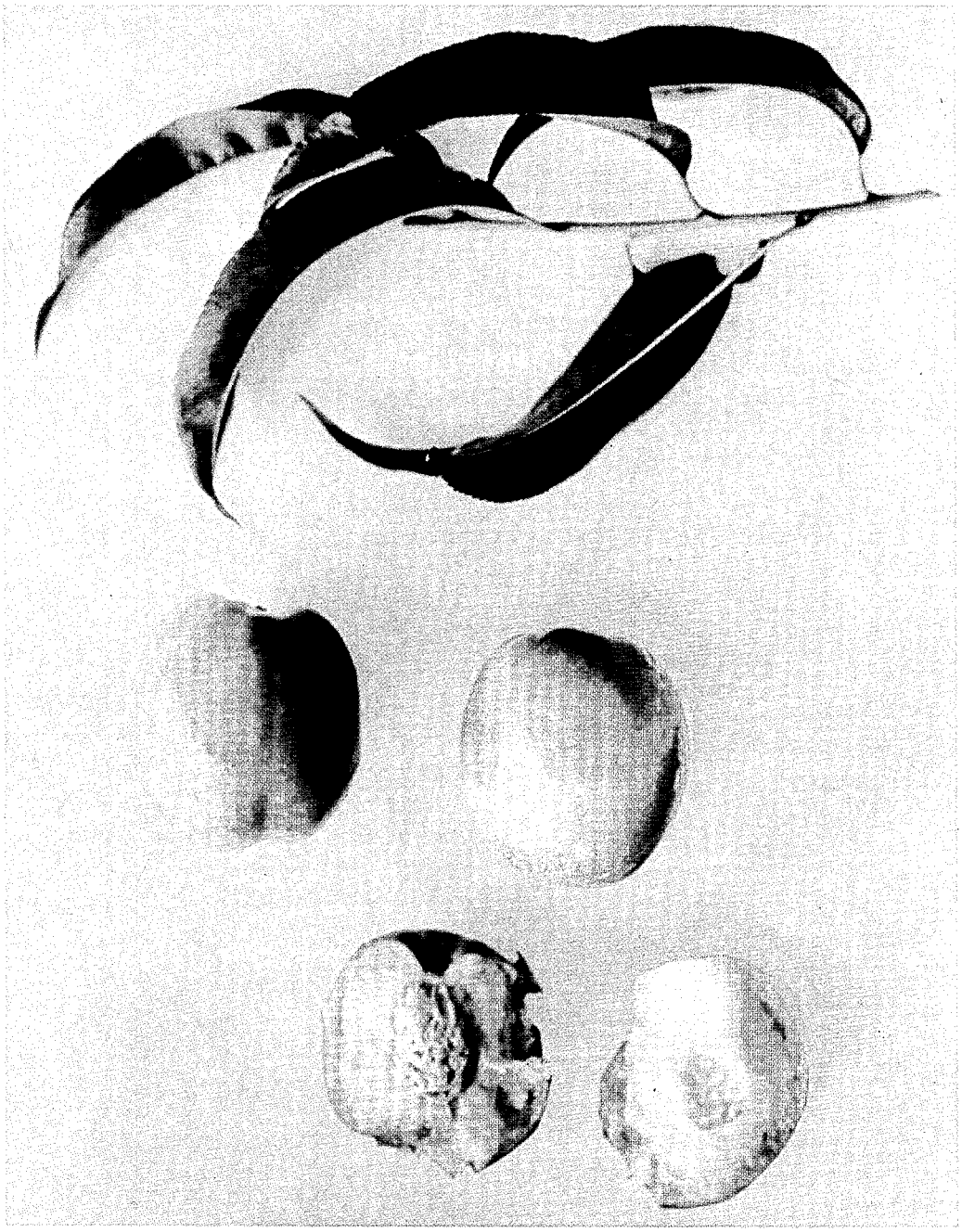

* * * * *